(12) United States Patent
Zigel et al.

(10) Patent No.: US 9,844,336 B2
(45) Date of Patent: Dec. 19, 2017

(54) APPARATUS AND METHOD FOR DIAGNOSING OBSTRUCTIVE SLEEP APNEA

(75) Inventors: Yaniv Zigel, Omer (IL); Ariel Tarasiuk, Meitar (IL); Nir Ben Israel, Tel Aviv (IL)

(73) Assignees: Ben Gurion University of the Negev Research and Development Authority, Beersheva (IL); Mor Research Applications Ltd., Tel Aviv (IL)

(*) Notice: Subject to any disclaimer, the term of this patent is extended or adjusted under 35 U.S.C. 154(b) by 383 days.

(21) Appl. No.: 13/818,104

(22) PCT Filed: Aug. 24, 2011

(86) PCT No.: PCT/IB2011/053715
§ 371 (c)(1),
(2), (4) Date: Feb. 21, 2013

(87) PCT Pub. No.: WO2012/025892
PCT Pub. Date: Mar. 1, 2012

(65) Prior Publication Data
US 2013/0184601 A1    Jul. 18, 2013

Related U.S. Application Data

(60) Provisional application No. 61/377,105, filed on Aug. 26, 2010.

(51) Int. Cl.
*A61B 5/00* (2006.01)
*A61B 7/00* (2006.01)
(52) U.S. Cl.
CPC .......... *A61B 5/4818* (2013.01); *A61B 5/7253* (2013.01); *A61B 7/003* (2013.01)

(58) Field of Classification Search
CPC ....... A61B 5/08; A61B 5/0816; A61B 5/0826; A61B 5/4806; A61B 5/4818
See application file for complete search history.

(56) References Cited

U.S. PATENT DOCUMENTS

2002/0099033 A1   7/2002   Meyer et al.
2005/0043645 A1   2/2005   Ono et al.
(Continued)

FOREIGN PATENT DOCUMENTS

WO     2010066008 A1   6/2010

OTHER PUBLICATIONS

PCT International Search Report PCT/IB2011/053715 dated May 8, 2012.
(Continued)

*Primary Examiner* — Charles A Marmor, II
*Assistant Examiner* — Thaddeus Cox
(74) *Attorney, Agent, or Firm* — A.C. Entis-IP Ltd.

(57) ABSTRACT

An embodiment of the invention provides a method of diagnosing obstructive sleep apnea, the method comprising: acquiring a sleep sound signal comprising sounds made by a person during sleep; detecting a plurality of snore sounds in the sleep sound signal; determining a set of mel-frequency cepstral coefficients for each of the snore sounds; determining a characterizing feature for the sleep sound signal responsive to a sum of the variances of the cepstral coefficients; and using the characterizing feature to diagnose obstructive sleep apnea in the person.

19 Claims, 2 Drawing Sheets

(56) References Cited

U.S. PATENT DOCUMENTS

| | | | |
|---|---|---|---|
| 2007/0215146 A1* | 9/2007 | Douglas et al. | 128/200.24 |
| 2007/0287896 A1 | 12/2007 | Derchak et al. | |
| 2008/0243014 A1 | 10/2008 | Moussavi et al. | |
| 2009/0234241 A1* | 9/2009 | Ota et al. | 600/529 |
| 2012/0004749 A1* | 1/2012 | Abeyratne et al. | 700/94 |

OTHER PUBLICATIONS

Supplementary European Search Report dated Aug. 4, 2014 for EP11819507 filed on Aug. 24, 2011.

Xu L, et al: "The optimization of perceptually-based features for speaker identification", May 23, 1989; May 23, 1989-May 26, 1989, May 23, 1989, pp. 520-523.

Udantha R. Abeyratne, et al: "Pitch jump probability measures for the analysis of snoring sounds in apnea; Snore sounds in OSA", Physiological Measurement, Institute of Physics Publishing, Bristol, GB, vol. 26, No. 5, Oct. 1, 2005, pp. 779-798.

Zigel Y., et al: "Analysis of speech 1-13 signals among obstructive sleep apnea patients", Electronics Engineers in Israel, 2008. IEEEI 2008. IEEE 25th Convention of, IEEE, Piscataway, NJ, USA, Dec. 3, 2008, pp. 760-764.

* cited by examiner

APPARATUS AND METHOD FOR DIAGNOSING OBSTRUCTIVE SLEEP APNEA

RELATED APPLICATIONS

The present application is a US National Phase of PCT Application No. PCT/IB2011/053715, filed on Aug. 24, 2011, which claims the benefit under 35 U.S.C. §119(e) of U.S. Provisional 61/377,105 filed on Aug. 26, 2010, the disclosure of which is incorporated herein by reference.

TECHNICAL FIELD

Embodiments of the invention relate to detecting sleep apnea.

BACKGROUND

Obstructive sleep apnea (OSA) is a common disorder characterized by repetitive collapse or narrowing of the upper airway passages during sleep that impairs ventilation and disrupts sleep. Factors that contribute to upper airway collapse include reduced upper-airway dilator muscle activity during sleep, specific upper-airway anatomical features, decreased end-expiratory lung volume, ventilatory control instability, and sleep-state instability. A collapse or narrowing of the airway passages during sleep may result in total or near total cessation of breathing or a partial reduction of ventilation.

Total or near total cessation of breathing that lasts at least ten seconds is referred to as "apnea", and typically results in neurological arousal of the person from sleep that initiates activity to reopen the upper airway passages and reestablish breathing. A partial obstruction of the airway passages can lead to a partial reduction of normal airflow during breathing by at least 50% for at least ten seconds, and is accompanied by oxygen desaturation of blood by at least 4%, and/or arousal from sleep is referred to as "hypopnea". In a vast majority of cases OSA is accompanied by snoring, which is caused by vibration of soft tissue in the upper airway passages.

OSA is associated with an increased risk of cardiovascular disease, stroke, high blood pressure, arrhythmia and diabetes. Sleep fragmentation resulting from obstructive events can also increase a person's risk of being involved in an accident, such as a driving accident as a result of excessive daytime sleepiness and fatigue. Once diagnosed, a number of different therapies are available for treating OSA. The therapies include behavioral modification training, use of masks for introducing a flow of pressurized air into the throat to prevent collapse of tissue in the upper airway passages, and surgery to modify anatomical features of the airway passages that are responsible for OSA.

Diagnosis of OSA and determination of OSA severity are typically made with reference to an index referred to as an apnea-hypopnea index (AHI). The index is simply a count of the number of apnea and hypopnea events that a person exhibits per hour of sleep. An AHI index that is less than about 10 e/hr (events per hour) is usually considered clinically insignificant. An AHI index between about 10 e/hr and about 30 e/hr is considered to indicate a moderate case of OSA, and an AHI index greater than about 30, is considered to indicate a severe case of OSA.

Whereas the AHI index appears simple and straightforward, determining an AHI value for a patient generally involves performing a sleep study, referred to as polysomnography, (PSG) study. PSG is a relatively complicated and expensive procedure carried out in a sleep laboratory during the patient's overnight stay in the laboratory. PSG typically involves attaching a variety of sensors to the patient's body to track changes that occur in a battery of physiological activities and functions such as brain activity, eye motion, skeletal muscle activation, and heart rhythm during sleep. The waiting period for PSG has been reported to be a few weeks to more than a year in the United States.

SUMMARY

An aspect of an embodiment of the invention relates to providing a non-invasive method of diagnosing presence of obstructive sleep apnea (OSA) in a person by determining an index, hereinafter an "apnea diagnosing index" (ADI), for the person responsive to detection and processing of snoring sounds made by the person during sleep. In an embodiment of the invention, a value for ADI is determined as a function of a plurality of, optionally five, features F1, F2, F3, F4, and F5 that characterize snoring sounds and provides an indication of OSA that correlates with indications of OSA provided by the well-known apnea-hypopnea index (AHI). Optionally, the function is a linear function.

An aspect of an embodiment of the invention relates to providing at least one new feature that may be used to distinguish snoring sounds that are indicative of presence and/or severity of OSA and to provide a value for ADI. In an embodiment of the invention the at least one new feature comprises "mel-cepstability", which provides a measure of variance of mel-frequency cepstrum coefficients (MFCC) of snoring sounds exhibited during a sleep period. Optionally, the at least one new feature comprises an average of variances in energy of groups of snores sounded during the sleep period. In an embodiment of the invention, the at least one feature comprises a number of groups of snores sounded during the sleep period for which variance in group energy is greater than a predetermined threshold.

An aspect of an embodiment of the invention relates to providing a method of classifying severity of OSA responsive to values of the ADI. In an embodiment of the invention, the ADI provides an indication as to severity of OSA exhibited by a patient. Optionally, the ADI provides a classification of snoring sounds as not indicative of OSA, indicative of mild OSA, or indicative of severe OSA.

An aspect of an embodiment of the invention relates to providing apparatus, hereinafter referred to as an "ADITESTER", which is relatively easily and conveniently used, optionally in a home environment, to diagnose OSA. In an embodiment of the invention, ADITESTER comprises a microphone that registers sounds generated by a person and the person's environment during sleep and a computer system that processes the registered sounds to identify and process snoring sounds therein to provide a value for ADI There is therefore provided in accordance with an embodiment of the invention, a method of diagnosing OSA, the method comprising: acquiring a sleep sound signal comprising sounds made by a person during sleep; detecting a plurality of snore sounds in the sleep sound signal; determining a set of mel-frequency cepstral coefficients for each of the snore sounds; determining a characterizing feature for the sleep sound signal responsive to a sum of the variances of the cepstral coefficients; and using the characterizing feature to diagnose OSA in the person.

Optionally the method comprises: determining a plurality of groups of the snore sounds; determining a group feature for each of the groups; determining a characterizing feature for the sleep sound signal responsive to the group features;

and using the determined characterizing feature for the sleep sound signal to diagnose OSA in the person. Optionally, determining a group of snore sounds comprises determining a cluster of consecutive snore sounds in the detected snore sounds for which a time delay between any two temporally adjacent snore sounds is less than or equal to a predetermined time period. Additionally or alternatively, the time period is equal to about a minute.

In an embodiment of the invention, determining a group feature for each group comprises determining a measure of energy for each of the snore sounds in the group. Optionally, determining the group feature comprises using the determined energy measures to determine a measure of an average energy of the snore sounds in the group. Optionally, determining the group feature comprises using the measure of average energy to determine a variance of the measures of snore sound energies for the group. The method optionally comprises determining the characterizing feature of the sleep sound signal responsive to an average of the determined variances of the groups. Additionally or alternatively, determining a characterizing feature of the sleep sound signal optionally comprises determining a number of groups in the sound signal for which the variance is greater than a predetermined threshold variance.

In an embodiment the method comprises: determining a number of silent periods in the sleep sound signal that are indicative of substantially total suspension of breathing by the person; determining a characterizing feature of the sleep sound signal responsive to the number of determined silent periods; and using the characterizing feature to diagnose OSA in the person. The method optionally comprises: determining a pitch density for each of the plurality of snore sounds in the sleep sound signal; determining an average pitch density for the snore sounds; determining a characterizing feature of the sleep sound signal responsive to the average pitch density; and using the characterizing feature to diagnose OSA in the person.

In an embodiment of the invention, using the characterizing sleep sound feature to diagnose OSA comprises providing a classifier that provides an indication as to whether the person has OSA responsive to the determined characterizing feature of the sleep sound signal. In an embodiment of the invention, using the characterizing sleep sound feature to diagnose OSA comprises diagnosing severity of OSA. Additionally or alternatively, the indication provided by the classifier optionally comprises a figure of merit generated responsive to a linear function of the sleep sound characterizing feature. The method optionally comprises configuring the linear function so that the figure of merit is correlated with the apnea-hypopnia index (AHI).

There is therefore provided in accordance with an embodiment of the invention a method of diagnosing OSA, the method comprising: acquiring a sleep sound signal comprising sounds made by a person during sleep; detecting a plurality of snore sounds in the sleep sound signal; determining a plurality of characterizing features for the sleep sound signal, the features comprising: a first feature determined responsive to a sum of the variances of cepstral coefficients of the snore sounds; a second feature determined responsive to a measure of an average of variances in energies of snore sounds in groups of the snore sounds; a third feature determined responsive to a number of groups of snore sounds that have a variance in snore sounds energies greater than a predetermined variance; and using the determined features to diagnose OSA in the person. Optionally, using the features comprises providing a classifier that provides an indication as to whether the person has OSA responsive to the features. Optionally, the indication comprises a figure of merit generated responsive to a linear function of the features. The method optionally comprises configuring the linear function so that the figure of merit is correlated with the apnea-hypopnia index (AHI).

In an embodiment of the invention using the features comprises diagnosing severity of OSA. Optionally, the plurality of features comprises a fourth feature determined responsive to a number of silent periods in the sleep sound signal that are indicative of substantially total suspension of breathing by the person. In an embodiment of the invention, the plurality of features comprises a fourth feature determined responsive to an average pitch density for the snore sounds.

There is further provided in accordance with an embodiment of the invention, apparatus for diagnosing OSA, the apparatus comprising: a microphone for acquiring a sleep sound signal of a person; and a computer system configured to execute an instruction set that processes the sleep sound signal in accordance with an embodiment of the invention to diagnose OSA in the person. Optionally, the computer system is a cloud based computer system.

DETAILED DESCRIPTION

Figure 1:
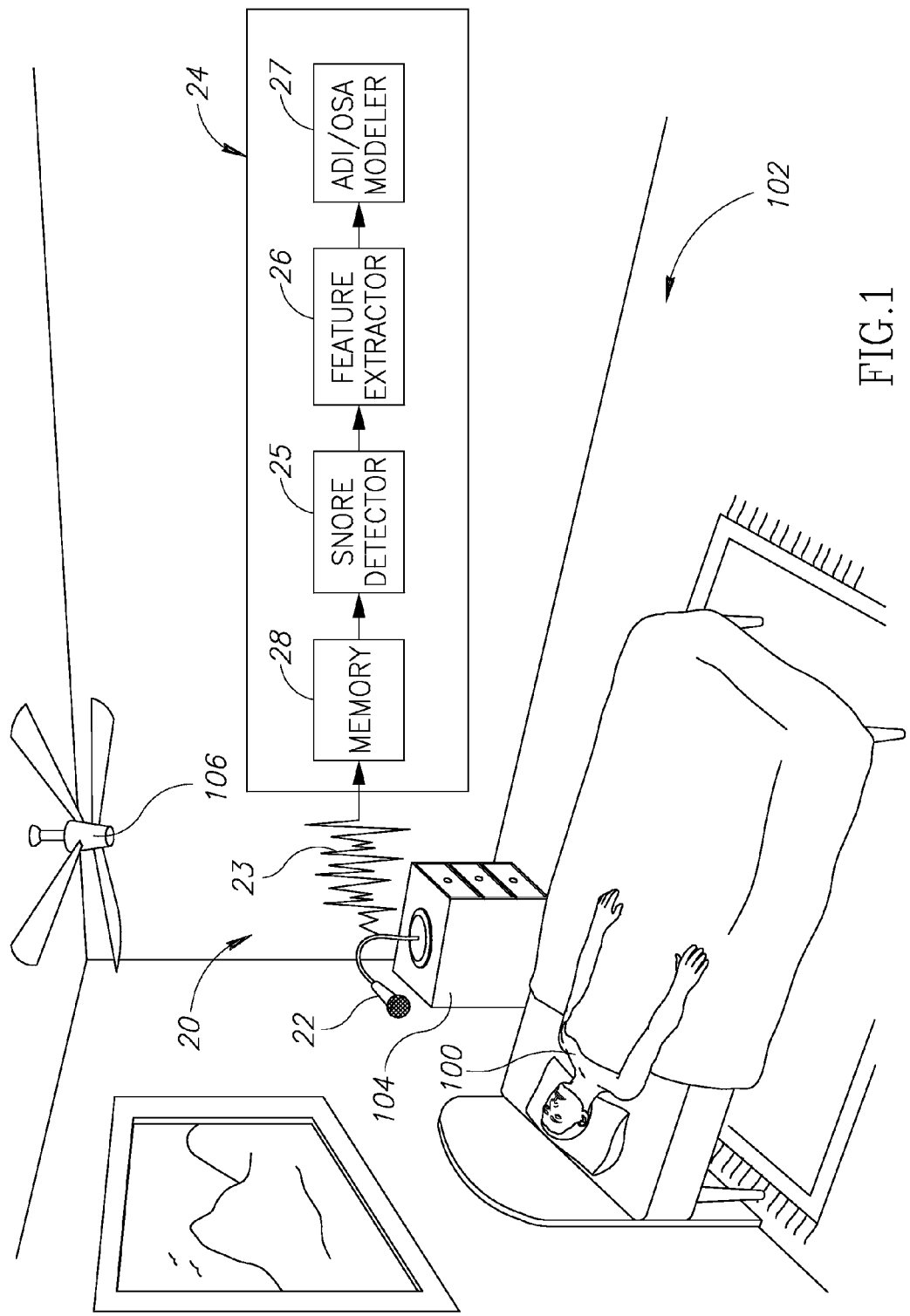
FIG. 1 schematically shows an ADITESTER in accordance with an embodiment of the invention.
Figure 2:
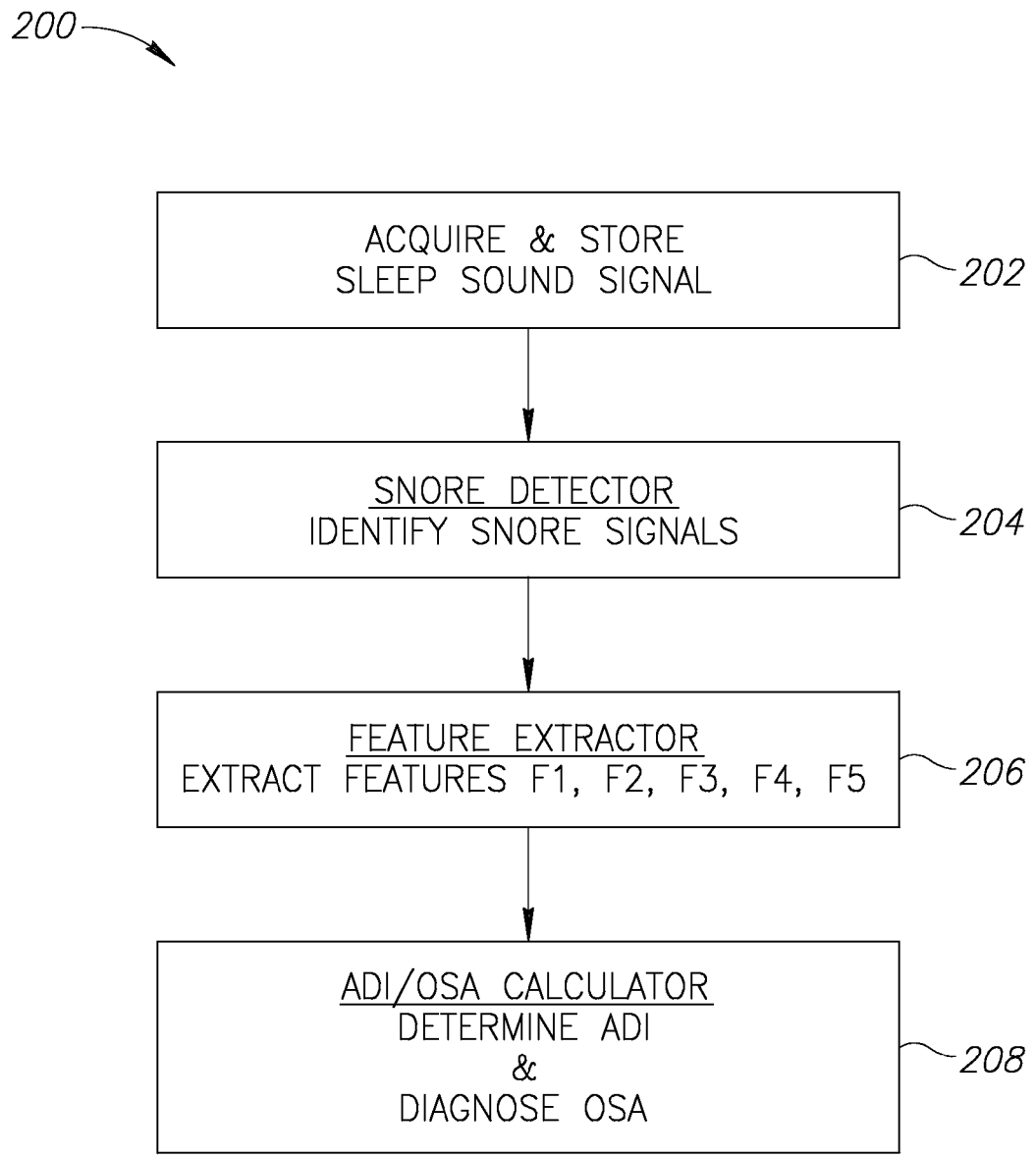
FIG. 2 schematically shows a flow diagram providing details of the operation of the an ADITESTER shown in FIG. 1, in accordance with an embodiment of the invention.

In the following detailed description an ADITESTER in accordance with an embodiment of the invention, is schematically shown in FIG. 1 and its components and operation are discussed with reference to the figure. The ADITESTER is shown being used to determine a value for ADI and therefrom a diagnosis for the presence and severity of OSA for a person responsive to snoring sounds that the person makes during sleep. Details of the operation of the ADITESTER in generating a feature set that characterizes the person's snoring sounds and determining an OSA diagnosis for the person in accordance with an embodiment of the invention are discussed with reference to a flow diagram shown in FIG. 2.

FIG. 1 schematically shows an ADITESTER 20 operating to determine possible presence and severity of OSA in a person 100 sleeping, optionally, in a bedroom 102 of his own house. ADITESTER 20 comprises a microphone 22, optionally placed on a night table 104 near person 100 and a computer system 24. Microphone 22 registers sounds made by the person during sleep and sounds that are not made by the person that reaches the microphone. Sounds that are made by the person comprise for example, snoring sounds, breathing, coughing and voice sounds, and sounds that are produced by motion of the person, such as bed creaking and blanket rustling sounds. Sounds that are not made by the person may comprise street sounds and sounds originating in other rooms of the person's house that reach the bedroom and sounds made by appliances, such as a whirring sound made by an overhead fan 106 in bedroom 102. Sounds not made by the person may also include sounds made by another person (not shown) in the bedroom. For convenience of presentation, sounds that are registered by microphone 22 that are not respiratory sounds (snoring and breathing sounds) made by person 100 are referred to as background sounds. Microphone 22 transmits the sounds that it registers as a "sleep sound signal" schematically represented by a waveform 23, to computer system 24.

Computer system 24 processes the sleep sound signal to identify snoring sounds therein and provide a value for ADI for the person responsive to the snoring sounds. The computer system is optionally configured having computer executable instruction sets referred to as a snore detector 25, a feature extractor 26, and an ADI/OSA modeler 27 and optionally comprises a memory 28 in which it stores sleep sound signal 23 that the computer system receives from microphone 22. Snore detector 25 processes the sleep sound signal stored in the memory to identify snoring sounds therein. Feature extractor 26 processes snoring sounds identified by snore detector 25 to determine features, in accordance with an embodiment of the invention, that characterize the snoring sounds and may be used to determine a value for ADI for person 100. ADI/OSA modeler 27 uses the features provided by the feature extractor to determine a value for ADI and therefrom a diagnosis as to presence and severity of OSA for person 100.

Computer system 24 may comprise a smart phone PC, a laptop, and/or a work book located in the home of person 100 that stores and executes the instruction sets defining snore detector 25, feature extractor 26, and ADI/OSA modeler 27. However, computer system 24 is not limited to being housed in a single computer, or a computer located in a same room with person 100. Computer system 24 may be a distributed system having components and executable instruction sets located in different servers, and may be partially or completely based on access to servers via the internet, that is partially or completely "cloud based". For example, memory 28 may be located close to microphone 22 and directly coupled to the microphone to receive and store sleep sound signal 23. Snore detector 25, extractor 26 and ADI/OSA modeler may be connected to memory 28 and each other by the internet and reside and function in different internet servers.

Aspects and functioning of ADITESTER 20, snore detector 25, feature extractor 26, and ADI/OSI modeler 27 in determining if person 100 suffers from OSA, and if so a severity of the OSA, are discussed below with reference to a flow diagram 200 shown in FIG. 2A.

In a block 202 ADITESTER 20 is turned on and microphone 22 is registering sounds made in or reaching room 102 and transmitting analog electronic signals that form sleep sound signal 23 to computer system 24. The computer system converts sound signal 23 from an analog signal to a digital signal and optionally stores the digital sleep sound signal in memory 28. Hereinafter, unless otherwise specified, reference to sleep sound signal 23 is assumed to reference the digital form of the sleep sound signal. Sleep sound signal 23 includes background sounds, such as background sounds noted above, and respiratory sounds made by person 100 during a period in which the person is asleep. A sleep period, for which an associated sleep sound signal 23 is acquired, may have different durations, and may of course have duration of a nominal full night's sleep of 6-8 hours. The sleep sound signal may include electromagnetic interference from power lines and appliances in a neighborhood of ADITESTER 20.

In a block 204, snore detector 25 processes sleep sound signal 23 to distinguish and identify snoring sounds in the sound signal. Any of various methods and algorithms may be used by the snore detector to identify snoring sounds. In an embodiment of the invention, snore detector 25 first filters sleep sound signal 23 to remove readily identifiable interference, such as electromagnetic interference generated at frequencies of alternating currents in power lines and appliance transformers, from sleep sound signal 23.

Thereafter, snore detector 25 processes the filtered sleep sound signal 23 to identify portions, hereinafter referred to as "audio events", of the filtered sleep sound signal 23 having energy and duration that indicate that the audio events are candidates for being "snore signals", which represent snoring sounds made by person 100. In an embodiment of the invention, for a portion of sleep sound signal 23 to be considered an audio event, the portion may be required to exhibit energy greater than a determined threshold energy $E_{th}$ and have a duration "$\tau_d$" greater than a minimum duration $\tau_{dmin}$ and less than a maximum duration $\tau_{dmax}$.

To determine a value for $E_{th}$ the sleep sound signal is segmented into consecutive, optionally partially overlapping sound frames having duration equal to about 30 ms (milliseconds). An energy for each sound frame is optionally, determined to be equal to a sum of squared amplitudes of sleep sound signal 23 in the frame, or an average of the squared amplitudes in the frame.

In an embodiment of the invention a value for $E_{th}$ is determined for each of a plurality of relatively long "windows" of time into which sleep sound signal 23 is divided responsive to lower and upper bound energies $E_L$ and $E_U$ respectively determined for sleep sound signal 23. A time window may have duration equal to hundreds or thousands of times that of the sound frames into which sleep signal 23 is segmented. Optionally $E_L$ and $E_U$ are determined from a frequency distribution of frames in the sleep sound signal as a function of frame energy. In an embodiment of the invention, $E_L$ is an energy greater than an energy at which the distribution is maximum and for which the distribution falls to a fraction of the maximum. Optionally, the fraction is equal to about 0.10. Optionally, $E_U$ is a multiple of $E_L$ determined to provide a reasonable upper limit to a value determined for $E_{th}$.

For a given time window, a candidate threshold energy "$CE_{th}$" for threshold energy $E_{th}$ of the window is determined from a frequency distribution of frames in the window as a function of frame energy. Optionally, $CE_{th}$ is an energy equal to a factor times an energy greater than an energy at which the frequency distribution is maximum, and for which the distribution falls to a fraction of its maximum. Optionally, the factor is equal to about 1.3. Optionally, the fraction is equal to about 0.10.

In an embodiment of the invention, the threshold energy $E_{th}$ for the given time window is set equal to $E_L$ if $CE_{th} < E_L$; is set equal to $E_U$ if $CE_{th} > E_U$; and is set equal to $CE_{th}$ if $E_L \leq CE_{th} \leq E_U$.

A portion of sleep sound signal 23 in a given time window is determined to be an audio event in accordance with an embodiment of the invention if the portion comprises a plurality of consecutive sound frames: that have cumulative duration $\tau_d$ satisfying the constraint $\tau_{dmin} \leq \tau_d \leq \tau_{dmax}$; that have a peak energy "$E_p$" greater than $E_{th}$; and for which none of the frames have energy less than a threshold energy "$E_r$". In an embodiment of the invention, $E_r$ is equal to $0.5(E_{th} + E_{Wm})$, where $E_{Wm}$ is a minimum energy exhibited by frames in the given window. Optionally, $\tau_{dmin}$ is equal to about 0.2 s (seconds) and $\tau_{dmax}$ is equal to about 2.5 s.

For each audio event that is determined to be a candidate snore signal, snore detector 25 generates a feature set and uses a Gaussian mixture model (GMM) classifier to determine responsive to the feature set, if the candidate snore signal is to be classified as a snore signal.

In an embodiment of the invention the feature set that snore detector 25 generates for a snore signal candidate comprises a set of "n" linear predictor coefficients (LPC), and the candidate's pitch density; average pitch value; total energy; duration, and rise time. Optionally, n is equal to 12. In an embodiment of the invention the GMM classifier comprises two Gaussian density models, one having order $n_S$ for snore signal candidates that represent snoring sounds and one having order $n_B$ for snore signal candidates that represent background sounds. Optionally, $n_S$ and $n_B$ are equal to 3 and 11, respectively. A set of GMM parameters that define the GMM classifier are optionally determined as a GMM parameter set that maximizes a likelihood of the feature sets for the models. The feature sets acquired for each of a plurality of training snore signal candidates that are known to represent a snoring sound or a background sound.

In a block 206 snore signals identified by snore detector 25 in sleep sound signal 23 acquired for person 100 are processed by feature extractor 26 to define a feature set for sleep sound signal 23 that may be used to provide a value for ADI and therefrom a diagnosis of OSA for the person, in accordance with an embodiment of the invention. In an embodiment of the invention, feature extractor 26 generates a feature set comprising five features, F1, F2, F3, F4, and F5, for sleep sound signal 23.

Feature F1, referred to as a "Mel-Cepstability" of sleep sound signal 23, is a function of mel-frequency cepstral coefficients (MFCC) determined from the log power spectra as functions of frequency measured in the mel-frequency scale of snore signals identified by snore detector 25 in sleep sound signal 23.

The mel scale is a perceptual scale of frequencies, measure in "mels", that maps frequency conventionally measured in Hz to a perceptual scale for which pairs of pitches having a same difference in mels are perceived by a human as having a same difference in frequency, or pitch. A frequency of 1000 Hz has a value in mels equal to 1000. A frequency "$f_{Hz}$" in Hz has a frequency $f_{mel}$ in mels defined by a formula:

$$f_{mel} = 2595 \log 10(1 + f_{Hz}/700). \quad (1)$$

Let an s-th snore signal of a total of "S" snore signals identified in sleep sound signal 23 acquired for person 100 have a time dependent amplitude represented by $A_s(t)$. Then a power spectrum $P(f_{Hz})$ of $A_s(t)$ as a function of frequency in Hz may be written:

$$P(f_{Hz}) = |F\{A_s(t)\}|^2, \quad (2)$$

where $F\{A_s(t)\}$ is a Fourier transform of $A_s(t)$. Filtering $P(f_{Hz})$ with a mel-frequency filterbank comprising K mel-frequency filters, provides a discrete mel-frequency power spectrum $P(k, f_{mel})$ for $A_s(t)$ having K values.

$$P(k, f_{mel}) = (MEL_k|F\{A_s(t)\}|^2), \quad k=1 \to K. \quad (3)$$

If $$X_k(s) = \{\log(MEL_k|F\{A_s(t)\}|^2)\}, \quad k=1 \to K, \quad (4)$$

then a discrete cosine transform (DCT) of the $X_k(s)$ generates optionally K mel-frequency cepstral coefficients $c_i(s)$ for $A_s(t)$, where $$c_i(s) = \Sigma_{k=1}^{k=K} X_k(s) \cos[i(k-\frac{1}{2})\pi/K], \quad i=1 \to K. \quad (5)$$

In accordance with an embodiment of the invention, feature F1, that is Mel-Cepstability, is a sum of the variances of the MFCC $c_i(s)$ optionally normalized to an average energy "E" of the S snore signals in sleep sound signal 23 acquired for person 100. In symbols, F1 may be defined by an expression, $$F1 = MelCepstability = \Sigma_{s=1}^{s=S} \Sigma_{i=1}^{i=K} [c_i(s) - \bar{c}_i(s)]^2/E. \quad (6)$$

In equation 6) $\bar{c}_i(s)$ is an average value for $c_i(s)$ over all S snore signals identified in sleep sound signal 23, and is defined by an expression, $$\bar{c}_i(s) = \Sigma_{s=1}^{s=S} c_i(s), \quad i=1 \to K. \quad (7)$$

If E(s) is the energy of the s-th snore signal then $$E(s) = \Sigma_{k=1}^{k=K} X_k(s)^2, \text{ and the average snore energy } E \text{ may be written} \quad (8)$$

$$E = (1/S)\Sigma_{s=1}^{s=S} E(s). \quad (9)$$

Feature F2 is optionally equal to an average of variances in energy for groups of snore signals in sleep sound signal 23. A group of snore signals in accordance with an embodiment of the invention comprises a sequence of snores in sleep sound signal 23 for which a time delay between an end of a snore in the group and a next subsequent snore in the group is less than or equal to a maximum time lapse "$\tau_g$". Optionally, 37 $\tau_g$ is equal to one minute.

Assume that sleep sound signal 23 comprises "G" snore signal groups, and a g-th group contains "$S_g$" snore signals. If the variation in snore signal energy in a given group g is varE(g), an average energy of snore signals in the group is $\bar{E}(g)$, and an s-th snore signal in the group has energy E(s, g), then $$varE(g) = \Sigma_{s=s_g}^{s=S_g}[E(s, g) - \bar{E}(g)]^2/S_g, \quad (10)$$

and if an average of varE(g) is $\overline{varE(g)}$, then $$F2 = \overline{varE(g)} = (1/G)\Sigma_{g=1}^{g=G} varE(g). \quad (11)$$

In an embodiment of the invention, feature F3 is equal to a number of snore groups in sleep sound signal 23 whose variance, varE(g), in the group energy is greater than a threshold variance, "$varE(g)_{TH}$." In symbols, $$F3 = \Sigma_{g=1}^{g=G} bool\{varE(g) > varE(g)_{TH}\}/G. \quad (12)$$

Feature F4 is a count $N_Q$ of a number of silent periods, referred to a "quiet hiatuses", which are indicative of substantially total suspension of breathing in sleep sound signal 23 that are located between two audio events, whether or not at least one of the audio events is classified as a snore signal. In accordance with an embodiment of the invention, to be considered a silent period an absence of sound from person 100 is required to have duration "$\tau_Q$" greater than a minimum duration "$\tau_{Qmin}$" and less than a maximum duration equal to "$\tau_{Qmax}$". In symbols, if $A(t)_S$ the time dependent amplitude of sleep sound signal 23, the F4 count $N_Q$ of quiet hiatuses may be defined by an expression:

$$F4 = N_Q = \Sigma_{s=1}^{s=S} bool\{(\tau_{Qmin} < \tau_Q < \tau_{Qmax}) | A_S(t) \leq A_{SB}\} \quad (13)$$

In an embodiment of the invention $\tau_{Qmin}$ is equal to about 10 seconds and $\tau_{Qmax}$ is equal to about 90 seconds. $A_{SB}$ is substantially equal to a background noise level that may exist when person 100 is not making any respiratory sounds.

Feature F5 is optionally equal to a mean of the pitch density of all snore signals identified in sleep sound signal 23 acquired for person 100. In an embodiment of the invention a pitch density for an s-th snore signal is determined by segmenting the snore signal into "F" frames having duration equal to 30 ms (milliseconds) and determining a maximum of an autocorrelation function for each frame. The pitch density PD(s) for the s-th snore signal is equal to a fraction of the frames in the snore signal for which a maximum of the autocorrelation function is greater than a threshold value "R". If the autocorrelation function of a given "f-th" frame in the s-th snore signal is represented by Rii(s,f) and a number of frames in the snore signal is equal to F, then, $$PD(s) = \Sigma_{f=1}^{f=F} bool\{MaxRii(s,f) > R\}/F, \quad (14)$$

and if an average of PD(s) over all snore sounds in sleep sound signal 23 is $\overline{PD}$, then $$F5 = \overline{PD} = \Sigma_{s=1}^{s=S} PD(s)/S. \quad (15)$$

In a block 208 ADI/OSA calculator 27 processes the features F1 ... F5 to generate a value for ADI. In an embodiment the invention, ADI is determined as a linear function of the features in accordance with an equation:

$$ADI = \alpha_o + \alpha_1 F1 + \alpha_2 F2 + \alpha_3 F3 + \alpha_4 F4 + \alpha_5 F5. \quad (16)$$

Optionally coefficients $\alpha_o \ldots \alpha_5$ are determined to provide a best fit to measurements of AHI acquired for a training group of persons that includes persons who do not exhibit OSA and persons who exhibit OSA characterized by different degrees of severity. Optionally values for AHI for the persons are determined from PSG studies. A best fit is optionally determined by a least squares analysis.

By way of a numerical example, features F1, F2, F3, F4, and F5 as defined above may assume values in the following ranges:

$$F1: [0 \text{ to } 0.5], F1: [0 \text{ to } 1.5], F1: [0 \text{ to } 1], F1: [0 \text{ to } 500], \text{ and } F1: [0 \text{ to } 1]. \quad (17)$$

Best fit values for $\alpha_o \ldots \alpha_5$ determined from a training group of about 90 people may have values, $$\alpha_o = -3, \alpha_1 = 128.1, \alpha_2 = 18.8, \alpha_3 = 14.9, \alpha_4 = 0.0075, \text{ and } \alpha_5 = -48.0143. \quad (18)$$

ADI determined in accordance with equation 16) for the numerical values given in expressions 17) and 18) was found to be able to distinguish whether a person had: no or a clinically insignificant case of OSA; a mild case of OSA (AHI index greater than 10 and less than 30); or a severe case of OSA (AHI index greater than 30). Classification of OSA using ADI in accordance with an embodiment of the invention was found to agree well with classifications provided by values of AHI determined by PSG.

The confusion matrix below indicates correlation between the ADI index determined in accordance with an embodiment of the invention and an AHI determined by PSG. Rows in the table are labeled with a diagnosis of OSA, "NO OSA", "MILD OSA", or "SEVERE OSA", determined by PSG. For each row, a diagnosis of OSA determined in accordance with the ADI index is given in columns headed "NO OSA", "MILD OSA", or "SEVERE OSA". From the matrix it is seen that the ADI and AHI indices give a same diagnosis 87% of the time for people with no OSA and 84% of the time for people with severe OSA. For mild cases of OSA agreement falls to about 56% but the two indices will agree 78% of the time as to whether or not a person has OSA.

|  |  | ADI INDEX | | |
| --- | --- | --- | --- | --- |
|  |  | NO OSA | MILD OSA | SEVERE OSA |
| AHI INDEX | NO OSA | 0.87 | 0.10 | 0.03 |
|  | MILD OSA | 0.22 | 0.56 | 0.22 |
|  | SEVERE OSA | 0.05 | 0.11 | 0.84 |

It is noted that whereas in the above description of embodiments of the invention, a linear regression function is used to provide a value of ADI and a diagnosis of OSA, practice of embodiments is not limited to linear regression classifiers. Non linear regression functions, support vector functions of F1 ... F5, and any of various other regression methods may be used in accordance with an embodiment of the invention to detect and classify cases of OSA.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method of diagnosing obstructive sleep apnea (OSA), the method comprising:
    acquiring a sleep sound signal comprising sounds made by a person during sleep;
    detecting a plurality of snore sounds in the sleep sound signal;
    determining a set of mel-frequency cepstral coefficients for each of the snore sounds;
    determining a variance for each of the sets of mel-frequency cepstral coefficients;
    summing the determined variances;
    determining a characterizing feature for the sleep sound signal responsive to the sum of the variances of the cepstral coefficients; and
    using the characterizing feature to diagnose OSA in the person, wherein the characterizing feature comprises a numerical value used as an indication of severity of OSA, where a low value means no OSA or a clinically insignificant case of OSA, a medium value means mild OSA, and a high value means severe OSA.

2. A method according to claim 1 and comprising:
    determining a plurality of groups of the snore sounds:
    determining a group feature for each of the groups;
    determining a characterizing feature for the sleep sound signal responsive to the group features; and
    using the determined characterizing feature for the sleep sound signal to diagnose OSA in the person.

3. A method according to claim 2 wherein determining a group of snore sounds comprises determining a cluster of consecutive snore sounds in the detected snore sounds for which a time delay between any two temporally adjacent snore sounds is less than or equal to a predetermined time period.

4. A method according to claim 2 wherein the time period is equal to about a minute.

5. A method according to claim 2 wherein determining a group feature for each group comprises determining a measure of energy for each of the snore sounds in the group.

6. A method according to claim 5 wherein determining the group feature comprises using the determined energy measures to determine a measure of an average energy of the snore sounds in the group.

7. A method according to claim 6 wherein determining the group feature comprises using the measure of average energy to determine a variance of the measures of snore sound energies for the group.

8. A method according to claim 7 and comprising determining the characterizing feature of the sleep sound signal responsive to an average of the determined variances of the groups.

9. A method according to claim 7 wherein determining a characterizing feature of the sleep sound signal comprises determining a number of groups in the sound signal for which the variance is greater than a predetermined threshold variance.

10. A method according to claim 1 and comprising:
  determining a number of silent periods in the sleep sound signal that are indicative of substantially total suspension of breathing by the person;
  determining a characterizing feature of the sleep sound signal responsive to the number of determined silent periods; and
  using the characterizing feature to diagnose OSA in the person.

11. A method according to claim 1 and comprising:
  determining a pitch density for each of the plurality of snore sounds in the sleep sound signal;
  determining an average pitch density for the snore sounds;
  determining a characterizing feature of the sleep sound signal responsive to the average pitch density; and
  using the characterizing feature to diagnose OSA in the person.

12. A method according to claim 1 wherein using the characterizing sleep sound feature to diagnose OSA comprises providing a figure of merit as to whether the person has OSA that is a linear function of the sleep sound characterizing feature.

13. A method according to claim 12 and comprising configuring the linear function so that the figure of merit is correlated with an apnea-hypopnia index (AHI).

14. A method of diagnosing OSA, the method comprising:
  acquiring a sleep sound signal comprising sounds made by a person during sleep;
  detecting a plurality of snore sounds in the sleep sound signal;
  determining a set of mel-frequency cepstral coefficients for each of the snore sounds;
  determining a variance for each of the sets of mel-frequency cepstral coefficients;
  summing the determined variances;
  determining a plurality of characterizing features for the sleep sound signal, the features comprising:
    a first feature determined responsive to the sum of the variances of cepstral coefficients of the snore sounds;
    a second feature determined responsive to a measure of an average of variances in energies of snore sounds in groups of the snore sounds;
    a third feature determined responsive to a number of groups of snore sounds that have a variance in snore sounds energies greater than a predetermined variance; and
  using the determined features to diagnose OSA in the person, wherein the plurality of characterizing features are used to obtain a numerical value used as an indication of severity of OSA, where a low value means no OSA or a clinically insignificant case of OSA, a medium value means mild OSA, and a high value means severe OSA.

15. A method according to claim 14 wherein the indication comprises a figure of merit generated responsive to a linear function of the features.

16. A method according to claim 15 and comprising configuring the linear function so that the figure of merit is correlated with an apnea-hypopnia index (AHI).

17. A method according to claim 14 wherein the plurality of features comprises a fourth feature determined responsive to a number of silent periods in the sleep sound signal that are indicative of substantially total suspension of breathing by the person.

18. A method according to claim 14 wherein the plurality of features comprises a fourth feature determined responsive to an average pitch density for the snore sounds.

19. Apparatus for diagnosing OSA, the apparatus comprising:
  a microphone for acquiring a sleep sound signal of a person; and
  a computer system configured to:
    detect a plurality of snore sounds in the sleep sound signal;
    determine a set of mel-frequency cepstral coefficients for each of the snore sounds;
    determine a variance for each of the sets of mel-frequency cepstral coefficients;
    summing the determined variances;
    determine a characterizing feature for the sleep sound signal responsive to the sum of the variances of the cepstral coefficients; and
    use the characterizing feature to diagnose OSA in the person, wherein the characterizing feature comprises a numerical value used as an indication of severity of OSA, where a low value means no OSA or a clinically insignificant case of OSA, a medium value means mild OSA, and a high value means severe OSA.

* * * * *